US008318903B2

(12) United States Patent
Dong et al.

(10) Patent No.: US 8,318,903 B2
(45) Date of Patent: Nov. 27, 2012

(54) BENIGN SOLVENTS FOR FORMING PROTEIN STRUCTURES

(75) Inventors: Bin Dong, Cleveland, OH (US); Olivier Arnoult, Shaker Heights, OH (US); Gary Wnek, Cleveland, OH (US); Lingui Meng, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 12/571,043

(22) Filed: Sep. 30, 2009

(65) Prior Publication Data
US 2010/0228011 A1    Sep. 9, 2010

Related U.S. Application Data

(60) Provisional application No. 61/194,685, filed on Sep. 30, 2008.

(51) Int. Cl.
*A61K 38/17* (2006.01)
*C09H 1/00* (2006.01)
(52) U.S. Cl. ........................................ 530/356; 530/354
(58) Field of Classification Search .................. None
See application file for complete search history.

(56) References Cited

U.S. PATENT DOCUMENTS 6,905,886 B2 * 6/2005 Sundaram et al. ............ 436/534
2004/0110664 A1 * 6/2004 Havelund et al. ................. 514/3

OTHER PUBLICATIONS

Jones et al. "Protein Composition of Proso Millet", J. of Agriculture and Food Industry, 1970, 18(1):37-39.*
Cole C.G.B., Gelatin. Frederick J Francis, editor. Encyclopedia of Food Science and Technology, 2nd edition. 4 Vols. New York: John Wiley & Sons, 2000. 1183-1188.*

* cited by examiner

*Primary Examiner* — Suzanne M Noakes
(74) *Attorney, Agent, or Firm* — Ulmer & Berne LLP

(57) ABSTRACT

A benign solvent for dissolving proteins comprises alcohol, salt and water. The ratio by volume of water to alcohol is between about ninety-nine-to-one and about one-to-ninety-nine. A salt concentration is between near zero moles per liter and the maximum salt concentration soluble in water. The amount of protein by weight as compared to the mixture of water and alcohol is between near zero percent and about 25 percent. A method for forming a protein structure from a benign solvent comprises forming a benign solvent from water, alcohol, and salt; and dissolving a protein in the benign solvent to form a protein solution. The method further comprises extracting the protein from the protein solution; and arranging the protein into a protein structure.

40 Claims, 11 Drawing Sheets

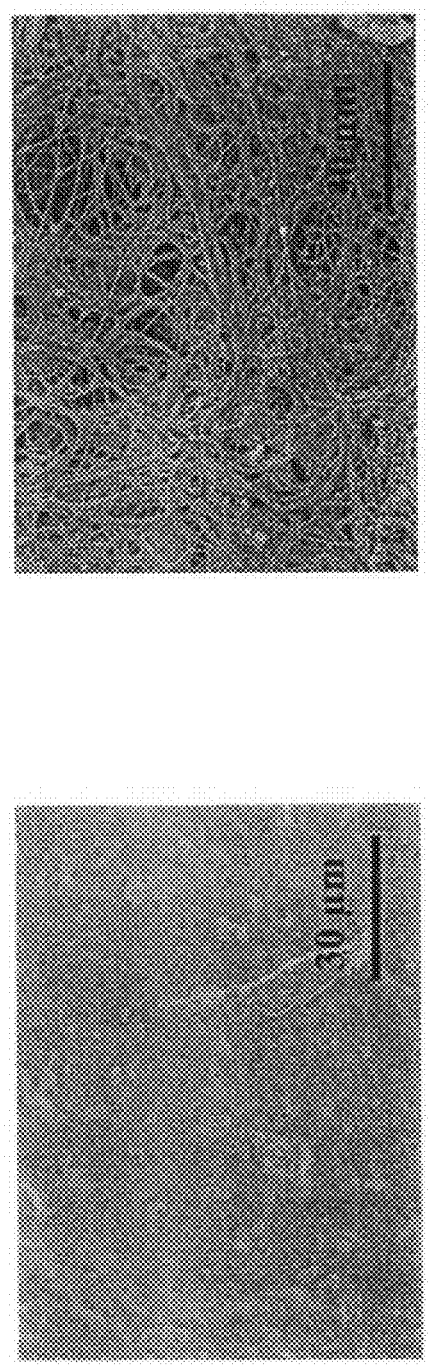
Figure 3A
Figure 3B
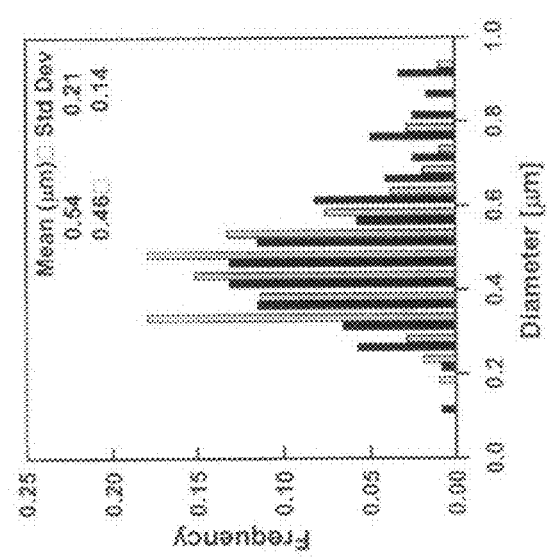
Figure 3C

BENIGN SOLVENTS FOR FORMING PROTEIN STRUCTURES

PRIORITY CLAIM

This application claims priority to and the full benefit of U.S. Provisional Patent Application Ser. No. 61/194,685 filed Sep. 30, 2008, and entitled "ELECTROSPINNING OF FIBER SCAFFOLDS," which is incorporated by reference as if fully rewritten herein.

TECHNICAL FIELD

The disclosed material relates generally to forming protein structures from a solution of protein dissolved in a benign solvent and more particularly to forming biocompatible protein structures from a solution of protein dissolved in a benign solvent.

BACKGROUND

Products and devices constructed from man-made materials can be implanted into or applied onto a human body to treat injuries, diseases, and other conditions of the human body. The materials chosen for such products or devices can be important for the product or device to successfully treat conditions of the human body. For instance, the compatibility of a material with the human body can determine if the product or device can be positioned on or in the human body. Products or devices can be made from synthetic material. However, if the synthetic material is dissimilar to human tissue, the success of the product or device can be limited. Products and devices constructed from naturally occurring materials such as proteins can provide biocompatible products or devices for implantation into or applying onto the human body to treat conditions of the human body.

SUMMARY

A benign solvent for dissolving proteins comprises alcohol, salt and water. The ratio by volume of water to alcohol is between ninety-nine-to-one and one-to-ninety-nine. A salt concentration is between near zero moles per liter and the maximum salt concentration soluble in water. The amount of protein by weight as compared to the mixture of water and alcohol is between near zero percent and about 25 percent.

A method for forming a protein structure from a benign solvent comprises forming a benign solvent from water, alcohol, and salt; and dissolving a protein in the benign solvent to form a protein solution. The method further comprises extracting the protein from the protein solution; and arranging the protein into a protein structure.

The method for forming a protein structure from a benign solvent further comprises electrospinning the protein solution to extract protein from the protein solution.

The method for forming a protein structure from a benign solvent further comprises electrospraying the protein solution to extract protein from the protein solution.

The method for forming a protein structure from a benign solvent further comprises using a gravitational feed method to extract protein from the protein solution.

BRIEF DESCRIPTION OF THE DRAWINGS

Objects and advantages together with the operation of the invention may be better understood by reference to the detailed description taken in connection with the following illustrations, wherein:

FIG. 3A is an SEM image of an electrospun fiber scaffold;
FIG. 3B is an SEM image of an electrospun fiber scaffold;
FIG. 3C is a chart showing electrospun fiber diameter distribution.

DETAILED DESCRIPTION

Figure 1:
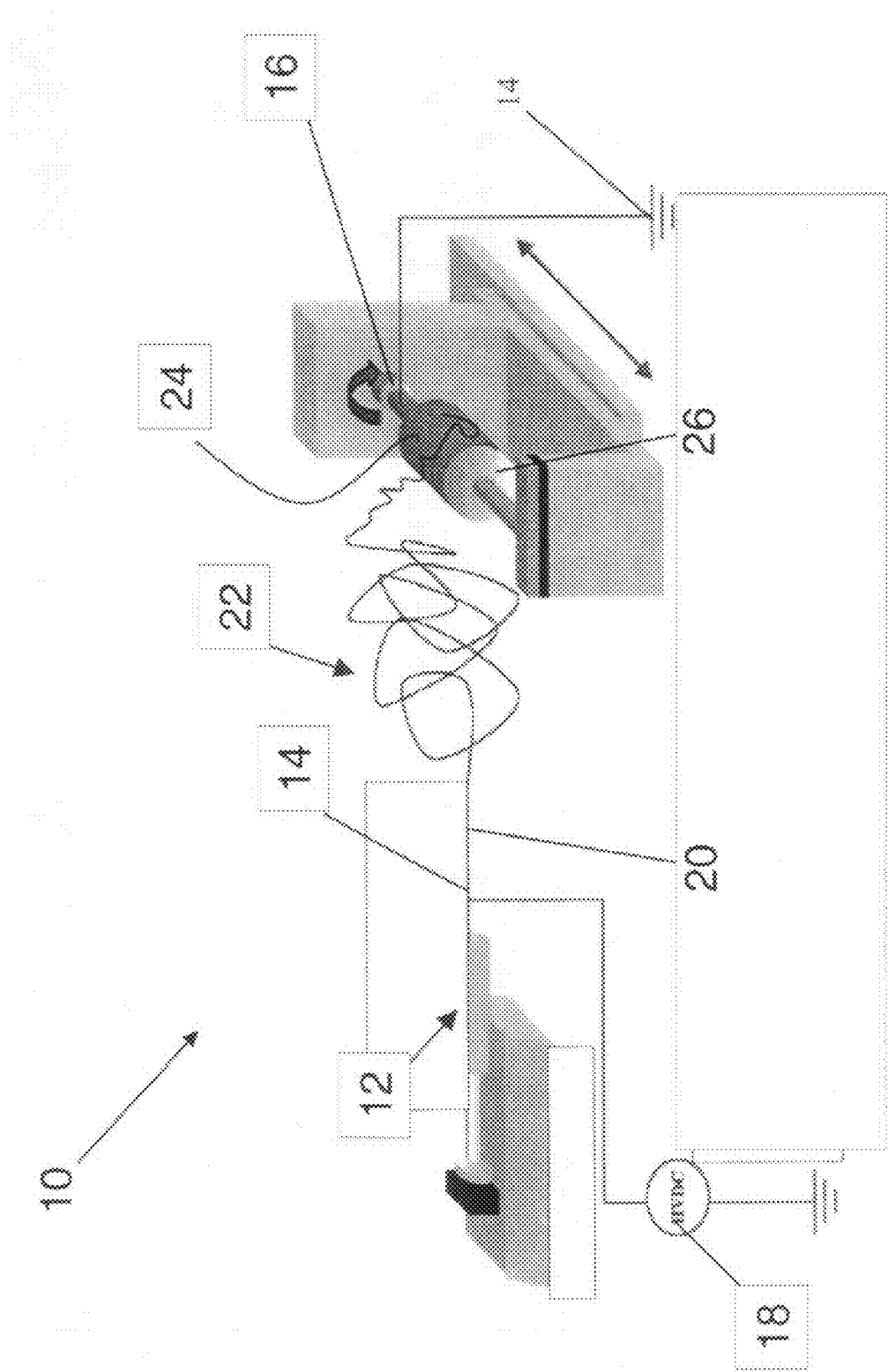
FIG. 1 is a schematic illustration of apparatus for electrospinning protein fibers from a protein solution.

The apparatuses and methods disclosed in this document are described in detail by way of examples and with reference to the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be and should not be construed as mandatory or limiting unless specifically designated as such. Selected examples of apparatuses and methods for forming biocompatible protein structures from a solution of protein dissolved in a benign solvent are hereinafter disclosed and described in detail with reference made to FIGS. 1-13.

Naturally occurring materials are good candidates for products and devices that are intended for use with biological material such as human and animal tissue. One category of materials that can be compatible with the biological material is natural polymers such as proteins. Examples of such biocompatible proteins include, but are not limited to, collagens, gelatin, elastin, fibrinogen, silk, and other suitable proteins. Such proteins can be used to form protein structures for implantation into or application onto a human body. Other materials that are generally biocompatible are polysaccharides such as hyaluronic acid, chitosan, and derivatives of starch and cellulose such as hydroxypropyl methyl cellulose phthalate, deoxyribonucleic acid (DNA), and ribonucleic acid (RNA).

One example of a protein structure that can be useful in forming products and devices for the human body is a scaffold or porous mat formed from protein fibers. Protein fibers can be used to construct a scaffold or porous mat structure that mimics an extra cellular matrix (ECM) of human tissue. Natural ECM generally has an open and porous structure. As will be described herein, fibers formed from proteins and joined into a matrix can simulate such an open and porous structure. Such a protein structure can be used in tissue engineering or wound care as a substrate for growing cells and/or tissue.

In another example, proteins can be used to form structures such as, for example, generally spherical agglomerates. Such agglomerates can be formed in a variety of sizes, ranging from submicron diameters to several hundred micrometers in diameter. Because of the compatibility of proteins with human tissue, protein agglomerates can be successfully implanted in or passed through the human body to affect treatment of a medical condition. For example, protein agglomerates can function as a component in a drug delivery system. A drug or other useful chemical compound can be attached to or inserted into a protein agglomerate. The protein agglomerate can then be passed through the human body, including through the blood stream, to a desired location where the drug can be released. In another example, protein agglomerates can function as structural or supportive components in the human body. For instance, protein agglomerates can be used in cosmetic medicine. Protein agglomerates can be injected under the skin to support the skin and smooth out wrinkles.

One method of forming a protein structure begins with dissolving a protein such as collagen in a solvent. Once dissolved, the protein can be extracted from the solvent and organized into a protein structure. One common solvent is 1,1,1,3,3,3 hexafluoro-2-propanol (HFP). However, any protein structure produced using such a solvent can have limited usefulness because of health concerns. For example, the United States Food and Drug Administration (FDA) has strict guidelines as to the amount of HFP allowed in a device or product intended for use with the human body. Because of strict FDA guidelines and general health concerns, using a solvent with benign characteristics for dissolving proteins or other biocompatible materials can yield biocompatible structures for implantation into or application onto a human body. Generally, a benign solvent is a solvent that either reduces health risks to a human body or is of minimal risk to the health of a human body.

One example of a benign solvent for dissolving protein comprises water, alcohol, and salt. The protein can be a Type I collagen, the alcohol can be ethanol, and the salt can be sodium chloride (NaCl). The association between water molecules, salt, and alcohol creates a complex structure in which proteins such as collagen are substantially soluble. Collagen is insoluble in most solvents because of interpeptide interaction. Collagen is substantially soluble in suitable water-alcohol-salt benign solvents because the properties of the solvents screen interpeptide interaction that usually results in insolubility of collagen. For example, the electrostatic interaction between the salt and the carbonyl group of the hydrophilic part of collagen and the hydrophobic interaction between the hydrocarbon chain of ethanol and the hydrophobic part of collagen can screen such interpeptide interaction. In general, any molecule or complex that exhibits a hydrophilic part and a hydrophobic part spaced by approximately the same distance as the hydrophilic part and hydrophobic part of the collagen molecule can dissolve collagen.

Although examples described herein include Type I collagen, it will be understood that all collagens—Type II, Type III, and so on—can be used in forming a protein structure for use with human tissue.

Generally, in suitable water-alcohol-salt solvents, the ratio of water to alcohol can range from a volume ratio of about 99:1 to about 1:99, the salt concentration can range from near 0 moles per liter (M) to the maximum salt concentration soluble in water, and the amount of protein by weight (as compared to the solvent) can range from near 0 percent to about 25 percent. In one example, the benign solvent comprises about a one-to-one ratio of water to ethanol and a salt concentration of about 3 M NaCl. Collagen is dissolved in such a solvent until the solution reaches about 16 percent collagen by weight. In another example, the solution comprises semed S (principally collagen type I with a ca. 5 percent collagen type III) dissolved in a solvent comprising phosphate buffered saline (PBS) buffer and ethanol, where the buffer to ethanol ratio of about one-to-one by volume. The saline concentration in the PBS buffer can range from 5× to 20×. The collagen concentration can be for example about 16 percent as compared to the total weight of the PBS/ethanol solvent. In yet another example, the protein dissolved in the solvent can be gelatin. The solvent can comprise a PBS buffer with a salt concentration of 10× mixed with ethanol at a one-to-one ratio by volume. Gelatin can be dissolved until the amount of gelatin by weight is about 16 percent by weight.

When protein has been dissolved in a suitable water-alcohol-salt solvent to form a protein solution, suitable processing methods can be used to extract protein from the solution and form protein structures. As previously discussed, such protein structures can be implanted into or applied onto the human body to affect treatment of a condition. Examples of suitable processing methods include, but are not limited to, electrospinning, electrospraying, and gravitational feed methods.

In one example, electrospinning can be used to form a protein structure. An example of apparatus 10 for forming a protein structure by electrospinning protein dissolved in a benign water-alcohol-salt solution is schematically shown in FIG. 1. The electrospinning method can include placing the protein solution in a syringe 12. The syringe can include a metal needle 14. The protein solution in the syringe 12 can be charged by the application of an electrical potential between the metal needle 14 and a ground target 16 spaced a distance away from the metal needle 14. The electrical potential can be applied by charging the metal needle 14 with a voltage from a power supply 18. The electrical potential can be increased until the electrostatic forces in the protein solution overcome the surface tension at the tip of the metal needle 14. As this surface tension is overcome, a fine jet 20 of solution containing entangled protein chains can be drawn out of the metal needle 14. As the fine jet 20 travels through the air, at least a portion of the solvent evaporates, resulting in a protein fiber 22 that dries as it travels through the air. The dry protein fiber 22 can be collected on a surface 24 that is in contact with the ground target 16. As shown in FIG. 1, the surface 24 can be on a rotating cylinder 26. It will be understood that the electrical potential can be created using a direct current (DC) power supply or an alternating current (AC) power supply.

In one example, the protein solution can be placed in a 5 milliliter (ml) syringe equipped with a 21 gauge blunt needle. The syringe can be placed in a syringe pump. A rotating drum can be placed approximately 10 centimeters (cm) from the tip of the needle. The pump rate can be set to about 1 milliliter per hour (ml/h) and the electrical potential can be set to about 20 kilovolts (kV). The result of such a setup can include the formation of a scaffold or mat on the rotating drum containing randomly oriented fibers or quasi-aligned fibers. The electrospinning process parameters, such as flow rate, potential field, and needle-to-collector distance can be adjusted to produce a variety of results or to optimize the stability of the fine jet of solution during electrospinning.

In another example, a scaffold or mat can be electrospun from a solution of about 16 percent by weight of gelatin dissolved in a PBS (10×) and ethanol solution with a volume ratio of about one-to-one. A flow rate of about 1 ml/h, a potential field of about 20 kV, and a needle-to-collector distance of about 10 cm can produce a stable jet of gelatin drawn from the gelatin solution.

Electrospinning proteins such as collagen and gelatin can result in the spinning of fibers as shown in FIG. 1. Such fibers can be highly aligned or oriented when mats and scaffolds are formed. In one example, electrospinning may be used to draw out protein fibers and such fibers can be generally arranged in a matrix. Once the fibers are arranged in a matrix, the fibers can be cross-linked to mimic the structure of ECM. Once cross-linked, the formed mat or scaffold can be a non-water-soluble protein structure that is biocompatible with the human body and thus implantable into or applicable onto the human body.

As the mat or scaffold is being formed by electrospinning, the fibers can be arranged so that fibers overlay one another and are in contact with one another. While in such an arrangement, the physical structure of the mat or scaffold can be enhanced by cross-linking the protein fibers. In one example, end groups such as aldehyde, carbodiimide, or epoxy can facilitate the cross-linking of the protein fibers of the mat or scaffold. A carbodiimide such as 1-ethyl-3-(3-dimethylaminopropyl)carbodiimide hydrochloride (EDC) can cross-link collagen using N-hydroxysuccinimide (NHS) as a catalyst. An electrospun collagen mat can be immersed in a 200 mM EDC and NHS ethanol solution for approximately 4 hours to cross-link collagen fibers. Once cross-linked, the collagen mat or scaffold can be placed in a PBS and salt solution similar to the buffer described above. Such a step can remove any non-cross-linked collagen from the mat or scaffold. The mat and scaffold, which can mimic the extra cellular matrix of human tissue can now be used as a substrate to grow cells or tissue, or can be used as a covering for an open wound to promote growth of tissue of the wound.

Examples of methods for forming a protein mat or scaffold by electrospinning can include adjusting the protein's solubility in the benign solvent; adjusting the evaporation rate of the solvent; adjusting the viscosity of the solution; or adjusting the surface tension of the solution. In one example, the solubility of collagen is enhanced by the addition of a salt to a water and ethanol mixture with a generally neutral pH level. When about 5 percent by weight of NaCl is added to a water and ethanol mixture for an about 16 percent by weight collagen solution, substantially all collagen dissolves. In one example, the salt composition of a PBS buffer solution can be about 80 percent NaCl by weight, about 17.4 percent sodium phosphate anhydrate by weight, and about 2.4 percent potassium phosphate anhydrate by weight. In another example, collagen may be dissolved in a PBS buffer where the total salt concentration exceeds 5 percent by weight. The evaporation rate of the solvent can be increased by increasing the amount of alcohol as compared to water in the protein solution.

As will be understood, the pH level, temperature, type of collagen, and type and concentration of salt all influence the structure of collagen in the protein solution. For example, at low collagen concentrations and a pH level of about 7.4, the transition temperature of crystalline polymer to random coil polymer is about 45 degrees Celsius. The transition temperature can be independent of salt concentration for potassium chloride (KCl) and NaCl. There is a progressive decrease in precipitation of collagen, that is to say that collagen becomes more soluble, as more salt is added. Addition of salt results in destabilization of the precipitated collagen while the ionic strength increases with salt additions. Collagen solubility can increase even if it appears that the crystalline structure of collagen is maintained upon addition of salt.

Alcohol affects the solubility of collagen in the buffer and ethanol solution. Alcohol and collagen interaction is moderated by hydrocarbon chain length, with alcohol disrupting internal hydrophobic interactions in the collagen. With increased alcohol concentration, there is a progressive increase in molar destabilization of the crystalline collagen precipitated in an alcohol and potassium acetate buffer mixture at an acidic pH, for example, a pH of about 4.8. For single collagen molecules, structural stability is primarily a function of interpeptide hydrogen bonding and chain rigidity.

The addition of salt promotes the solubility of collagens. Hydrogen bonding between the hydrophilic part of collagen and water molecules can be too weak to break the interpeptide interaction, and the stronger electrostatic forces induced by salt in aqueous media may be necessary. The combination of both electrostatic and hydrophobic forces appears to interact strongly enough with the collagen chain to substantially dissolve the collagen in a mixture of ethanol and PBS buffer with an about one-to-one ratio when a salt concentration is at least about 5× in the buffer.

In addition to dissolving proteins such as collagens, the buffer and ethanol binary solvent can further facilitate the electrospinning process. The salt in the buffer as well as the alcohol can assists in overcoming the high surface tension of water that can partially inhibit spinnability of water based polymeric solution. In addition, the salt increases the charge density in the protein solution, which can facilitate the formation of a stable Taylor cone. The low evaporation rate of water, which can inhibit the formation of fibers during electrospinning, can be compensated for by the high evaporation rate of alcohol.

Figure 2B:
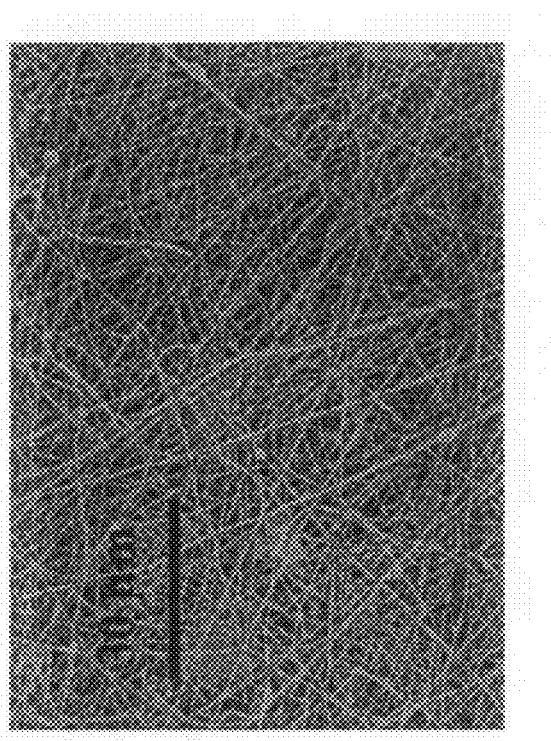
FIG. 2B is an SEM image of an electrospun fiber scaffold.
Figure 2A:
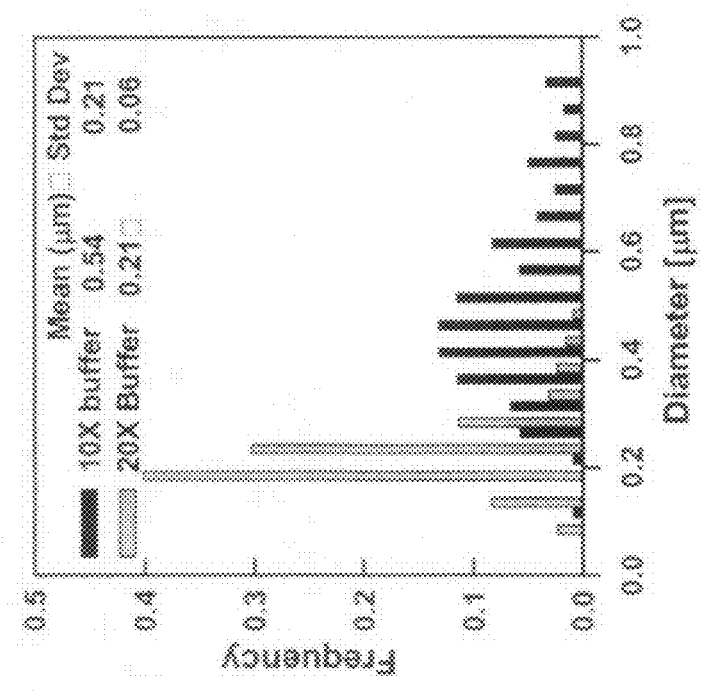
FIG. 2A is a chart showing electrospun fiber diameter distribution.

Electrospinning of collagen solutions with about a one-to-one volume ratio of ethanol to PBS (10× or 20×) can be stable and create fiber mats or scaffolds that exhibit relatively consistent fiber diameters. The increase of salt concentration in the PBS buffer can decrease the fiber diameter, and higher salt concentration can result in greater elongation of the electrospun jet due to higher density of repulsive charges in the Taylor cone. As is shown in the chart of FIG. 2A, increasing the salt concentration from 10× to 20× decreases the average fiber diameter from 540 micrometers to 210 micrometers but also significantly reduces the standard deviation of the fiber diameter distribution (from 210 micrometers to 60 micrometers). FIG. 2B is a scanning electron microscope (SEM) image of collagen fibers electrospun from PBS (20×) and ethanol.

As will be understood, cross-linking of protein mats or scaffolds facilitates the use of electrospun mats or scaffolds for regenerative or tissue engineering and wound care, because cross-linking promotes stability of the collagen mat or scaffold. In addition to mimicking the ECM of human tissue to promote cell or tissue growth, when collagens with hemostatic properties are used, application of a mat or scaffold over a new or existing wound can arrest blood flow from the wound and promote clotting.

Cross-linking can be facilitated by the presence of carboxyl groups on the hydrophilic part of collagens. FIGS. 3A and 3B illustrate cross-linking of fiber mats with EDC and NHS as a catalyst. Mats are immersed in an ethanol solution comprising EDC and NHS for four hours. The mats can then be immersed in a buffer solution containing the same salt concentration as the one the collagen was electrospun from to remove un-cross-linked fibers.

For the collagen mats shown in FIGS. 3A and 3B, the collagen fibers of the mat were cross-linked with EDC and NHS. The fibers were electrospun from a PBS (10×) and ethanol solution. FIG. 3A is an SEM image of a self-standing mat and FIG. 3B is a framed mat. FIG. 3C is a chart of the diameter distribution of cross-linked fibers electrospun from a PBS (10×) and ethanol mixture. As seen in FIG. 3B, the cross-linked mat may retain a porous and open structure upon cross-linking.

A collagen mat can be soaked in an ethanol solution such that the mat shrinks to form a film-like surface (shown in FIG. 3A). If shrinkage is not desired, frames can be placed on each side of the mat and clipped together to prevent the mat from shrinking when it is immersed in the ethanol solution. Such frames can be constructed of material that is easy to remove, such as Teflon. The fiber diameter distribution does not significantly change between non-cross-linked and cross-linked collagen when a frame is used. Therefore, the frame can efficiently prevent fiber shrinkage when immersed in ethanol.

Figure 4B:
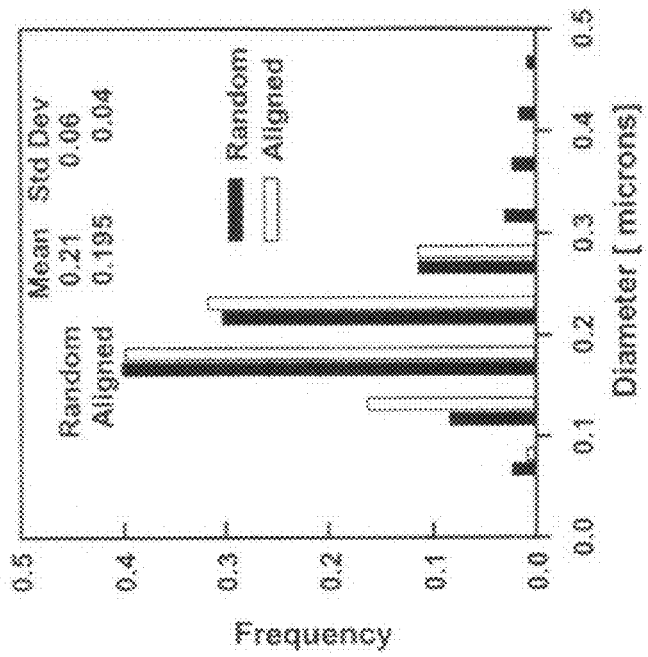
FIG. 4B is a chart showing electrospun fiber diameter distribution.
Figure 4A:
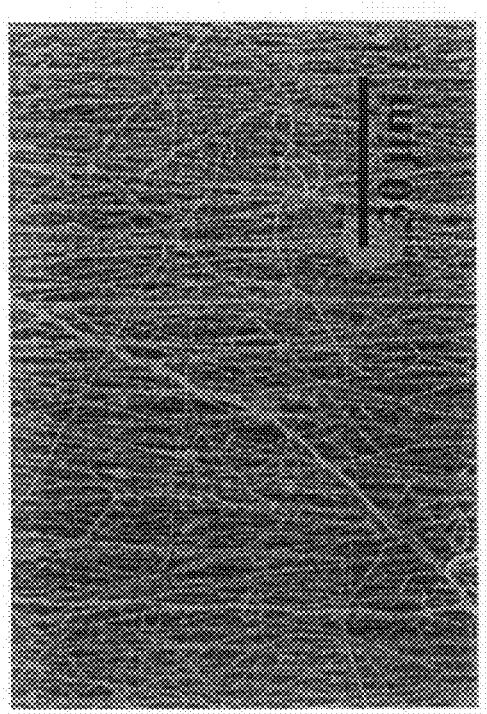
FIG. 4A is an SEM image of an electrospun fiber scaffold.

The architectural structure of protein mats or scaffolds can be important depending on the intended application of the mat or scaffold. For example, mats and scaffolds can be used to simulate types of human tissue. Aligned fibers may be useful in simulating a variety of tissue types including ligaments, nerves, cardiac tissues, and the like. The alignment of electrospun fibers may be controlled by the rotational speed of the rotating cylinder 26 shown in FIG. 1. If the speed of the cylinder matches or is faster than the speed of the jet of protein solution exiting the syringe, the protein fibers may be drawn out of the syringe in the loop direction of the cylinder. The orientation of protein fibers in the mat can be characterized by Herman's orientation function, which is:

$$f=(3*(\cos^2 \theta)-1)/2$$

where θ is the angle of the protein fibers compared to the loop direction of the drum. An optimally aligned fiber mat (that is to say, a mat where all the fibers all aligned in the same direction) will have a Herman's orientation function equal to 1. An optimally random configured fiber mat (that is to say, a mat where all the fibers are randomly aligned) will have a Herman's orientation function equal to −0.5. FIG. 4A shows an SEM image of a protein fiber mat, where the speed of the rotating drum matched the speed of the jet of protein solution. The mat was electrospun from a PBS (20×) and ethanol solution and has a Herman's orientation function equal to about 0.93. The mat shown has relatively highly oriented fibers. Because oriented fibers can be mechanically drawn, the fibers can have smaller diameters than randomly oriented fibers electrospun under similar conditions. However, as shown in FIG. 4B, for this particular mat, where the speed of the rotating drum matched the speed of the jet of protein solution, the drawn and aligned fibers do not show significantly smaller diameters than random fibers.

Figure 5B:
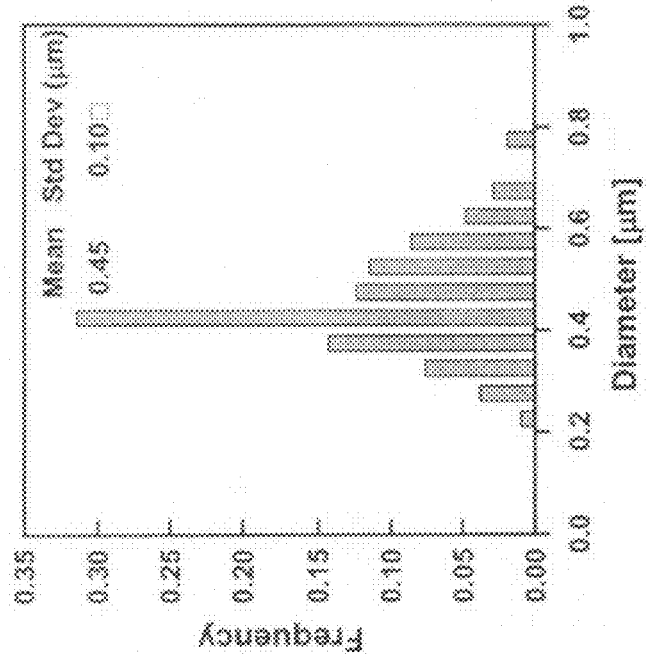
FIG. 5B is a chart showing electrospun fiber diameter distribution.
Figure 5A:
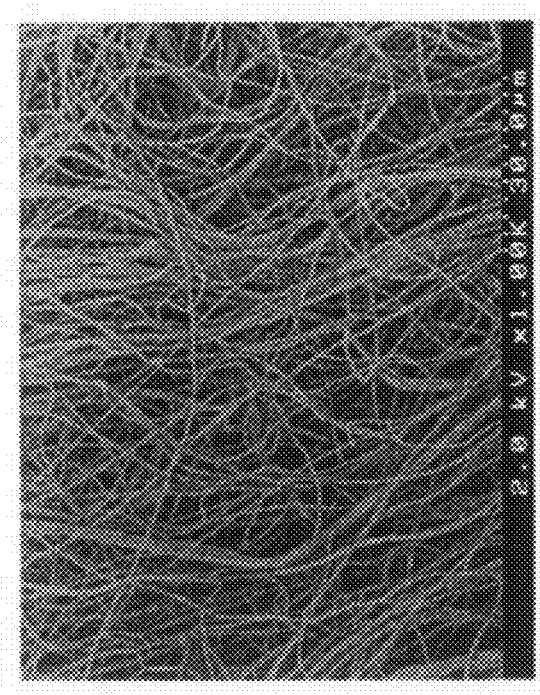
FIG. 5A is an SEM image of an electrospun fiber scaffold.

As previously discussed, gelatin may be electrospun from binary solutions and electrospinning conditions disclosed herein. For example, when a PBS (10×) and ethanol solution is used for dissolving gelatin at about 16 percent by weight, similar results are obtained as compared to collagen fibers. In addition, the gelatin can be cross-linked in a similar manner and under similar conditions as described for collagens. FIG. 5A shows a gelatin fiber mat and FIG. 5B shows a chart of the diameter distribution of the gelatin fibers.

Figure 6:
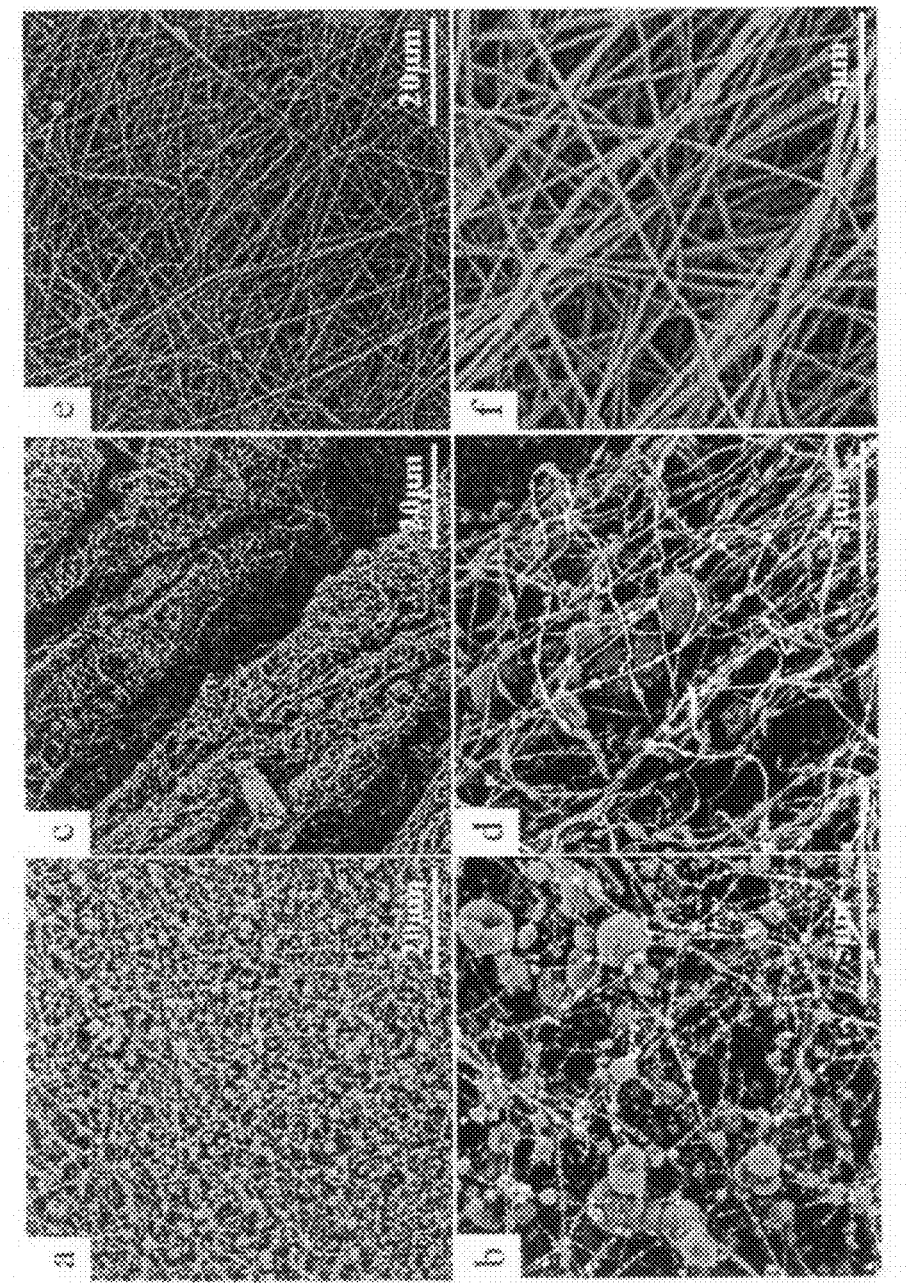
FIG. 6 is multiple SEM images of electrospun fiber scaffolds.
Figure 7:
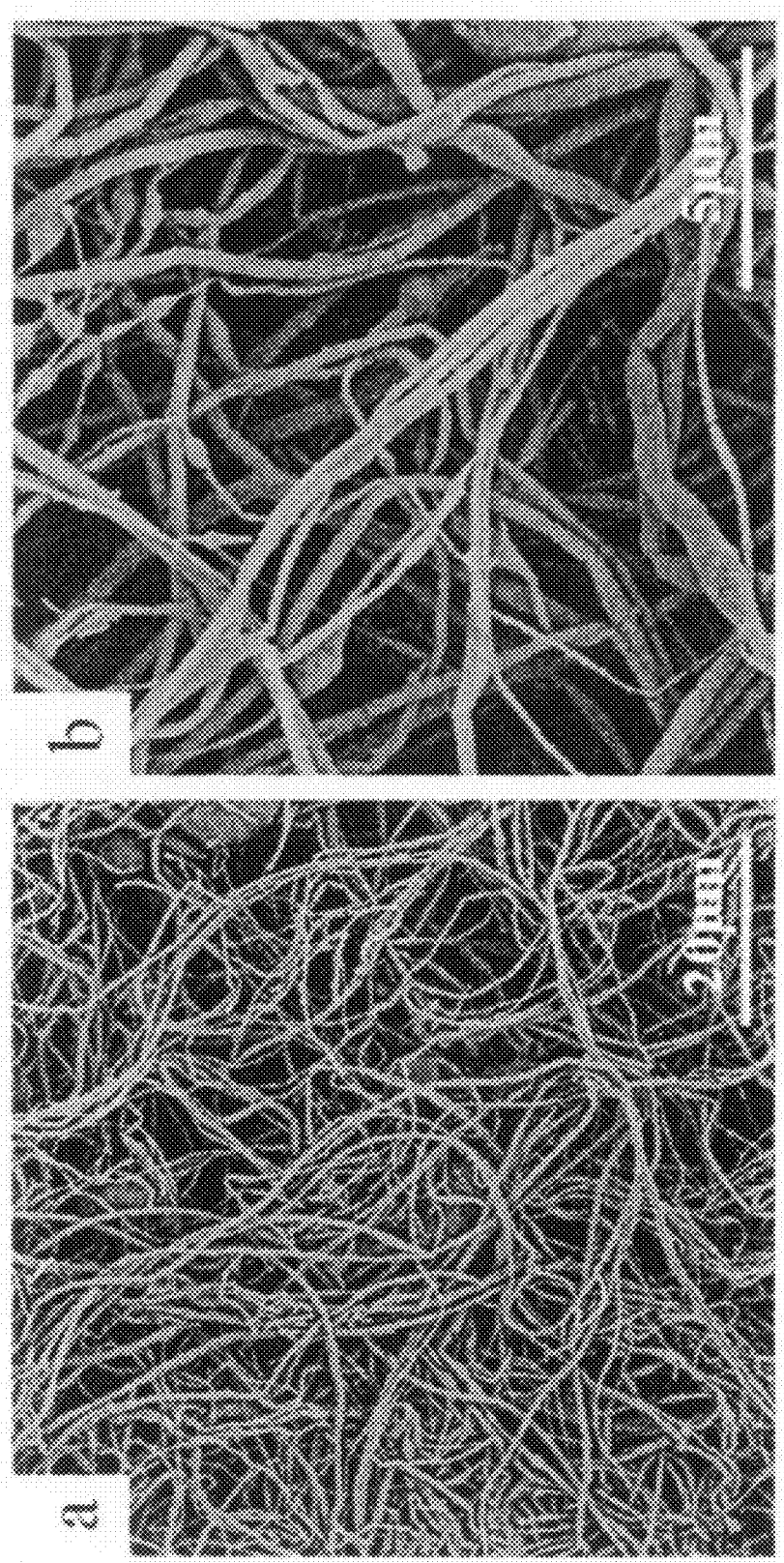
FIG. 7 is an SEM image of an electrospun fiber scaffold.

The concentration of collagen in the solution may affect electrospinning. Collagens readily dissolve in a solvent comprising a one-to-one ratio between PBS (20×) and ethanol. Generally, collagen solutions ranging from about 4 percent by weight to about 25 percent by weight can be electrospun. By controlling the concentration of collagen, different morphologies and fiber diameters can result. FIG. 6 includes several SEM images of morphologies resulting from electrospinning different concentrations of collagen dissolved in solutions. FIGS. 6a and 6b are different magnifications of a fiber mat electrospun from a solution with about 4 percent collagen by weight. As may be seen, generally the diameter of the fibers is inconsistent because the viscosity of the solution is low and does not generally form continuous fibers during electrospinning. FIGS. 6c and 6d are different magnifications of a fiber mat electrospun from a solution with about 10 percent collagen by weight. As the concentration of collagen is increased, the diameter of the fibers becomes more consistent because continuous fibers are more readily generated by a solution with about 10 percent collagen by weight. FIGS. 6e and 6f are different magnifications of a fiber mat electrospun from a solution with about 16 percent collagen by weight. As may be seen, submicron fibers of generally consistent diameter are formed.

The concentration of salt and ethanol can affect the solubility of collagens in water. Collagen can be generally insoluble at about 16 percent by weight in either PBS (20×) or ethanol. However, when a small amount of ethanol is added into PBS (20×) buffer to form a PBS (20×) to ethanol volume ratio of about nine-to-one, the collagen substantially dissolves into this mixture. By adding more ethanol into PBS (20×) buffer (that is, the volume ratio decreases from about nine-to-one to about seven-to-three to about one-to-one) there is generally no affect on the solubility of collagen. The collagen remains substantially soluble. However, when the PBS (20×) to ethanol volume ratio is reduced to three-to-seven, collagen is generally no longer soluble. Furthermore, the salt concentration affects the solubility of collagen when the water to ethanol volume ratio is held constant at about one-to-one. The salt concentration in 5×, 10× and 20×PBS buffer is sufficient to substantially dissolve collagen in the mixture solution.

The addition of salt and ethanol to the protein solution can facilitate the electrospinning of the polymer solution. As salt increases the conductivity and ethanol decreases the boiling point, concentrations of salt and ethanol affect the electrospinnability of solutions that are capable of dissolving collagen with PBS (20×) to ethanol ratio varying from about nine-to-one to about one-to-one. As seen in FIGS. 7a-7b, fibers may be formed from electrospinning collagen with PBS (20×) to ethanol volume ratios of about seven-to-three. In addition, collagen solutions with a PBS (20×) to ethanol volume ratio of about one-to-one demonstrate good electrospinability and a stable Taylor cone. Such a solution may be electrospun to form fibers and a mat as thick as about 150 microns.

In one example, the protein solution can include a cross-linking agent so that cross-linking of protein fibers occurs as the protein fibers are being electrospun. This reduces the formation and cross-linking of protein fibers to one general step. In such an example, the protein solution includes protein, water, alcohol, salt, and a cross-linking agent. A protein solution is formed by dissolving about 16 percent by weight of collagen in a solvent. The solvent comprises PBS buffer (20×) and alcohol. Prior to forming the solvent a cross-linker is added to the alcohol. The cross-linker can be about 200 mMoles of EDC and NHS at a ratio by weight of about one-to-one. The collagen solution can be deposited in a syringe equipped with a metal needle as previously described.

The protein solution is subjected to an electrical potential and electrospun to form a jet of protein solution and form a protein structure such as a mat or scaffold. In one example, a voltage of about 20 KV can be applied to the metal needle and the pump rate can be about 0.5 milliliters per hour. A rotating drum can be positioned about 10 centimeters from the needle to collect the electrospun mat.

Figure 8:
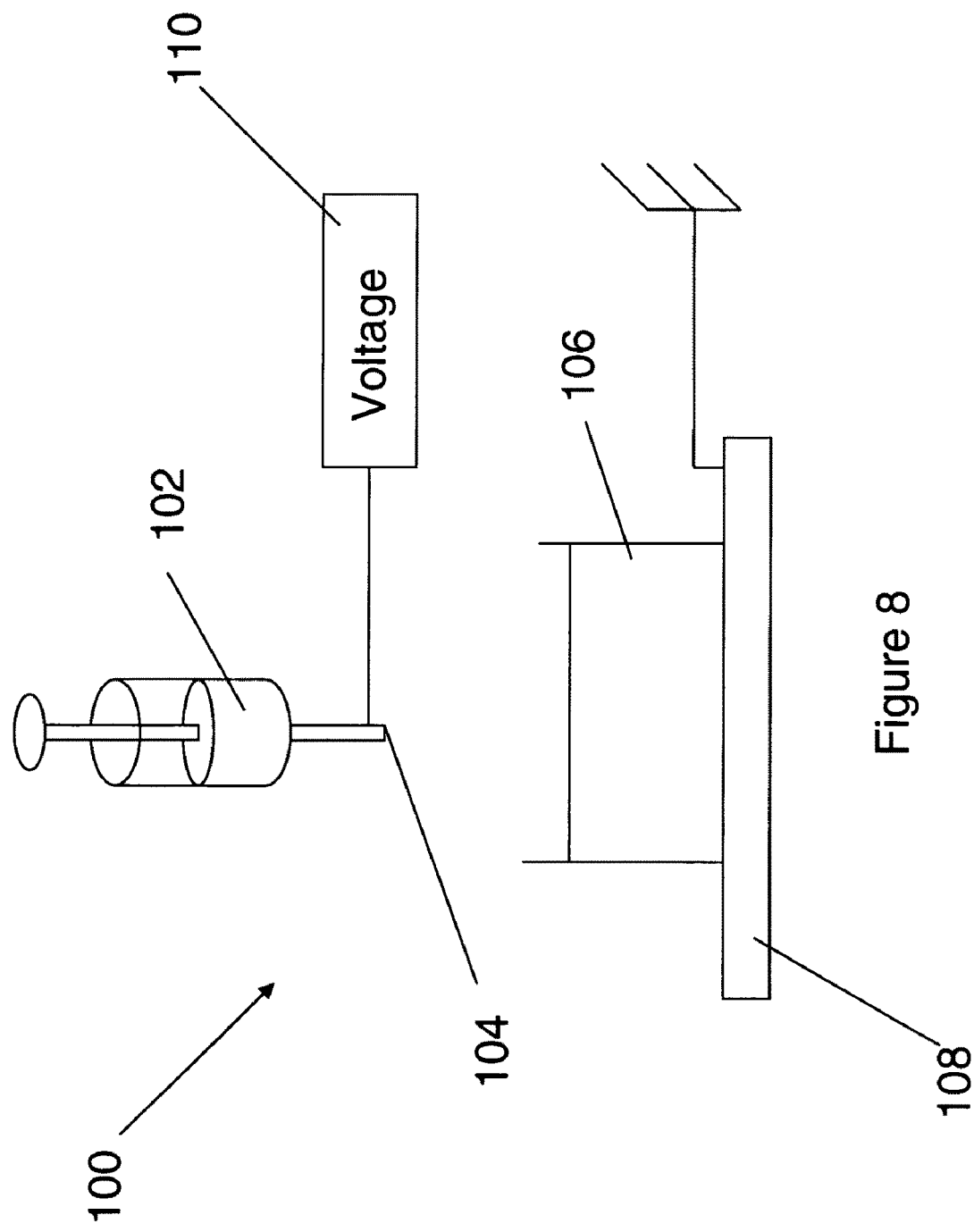
FIG. 8 is a schematic illustration of apparatus for electrospinning or electrospraying protein agglomerations from a protein solution.

Protein dissolved in benign solvents as described herein can be used to form protein agglomerates such as generally spherical particles or beads. An apparatus 100 for forming protein agglomerate is schematically shown in FIG. 8. Protein agglomerates can be formed using methods that include electrospinning, electrospraying, and gravitational feed methods. The apparatus 100 includes a syringe 102 equipped with a metal needle 104. The syringe 102 is suspended over a receptacle 106, and the receptacle 106 is positioned on a metal plate 108, which is grounded. A protein solution comprising protein dissolved in a water-alcohol-salt solvent as described herein is placed in the syringe 102. Similar to previous descriptions, an electrical potential can be applied to charge the protein solution by applying a voltage from a power supply 110 to the metal needle 104. A solution of a cross-linking agent such as EDC dissolved in a solvent such as ethanol can be placed in the receptacle 106.

Figure 9:
FIG. 9 is an SEM image of cross-linked agglomerations.

For electrospinning, the electrical potential can be increased to grow the electrostatic forces and overcome the surface tension at a tip of the needle 104. As this surface tension is overcome, a fine jet of protein solution containing entangled protein chains can be drawn out of the needle 104. As the fine jet travels through the air, the solvent evaporates leaving a dry protein fiber that engages the surface of the cross-linking solution in the receptacle 106. The impact of the protein fiber's engagement with the surface of the cross-lining solution fractures the fiber into relatively short sections. Upon entering the cross-linking solutions, each short section of protein fiber draws inward and cross-links with itself, resulting in a generally spherical protein agglomerate or bead. In one example, the protein solvent comprises about 16 percent collagen by weight dissolved in a solvent of about one-to-one ratio by volume of PBS buffer (20×) to ethanol. A flow rate of about 1 ml/h is applied to the protein solution in the syringe 102, a voltage of about 25 kV is applied to the metal needle 104, and the metal plate 108 is spaced about 20 cm from the tip of the metal needle 104. An cross-linking solution of EDC dissolved in ethanol is placed in the receptacle 106. Such parameters form cross-linked protein agglomerates as shown in FIG. 9. Such protein agglomerates can be, for example, more than 100 micrometers in diameter.

Figure 10:
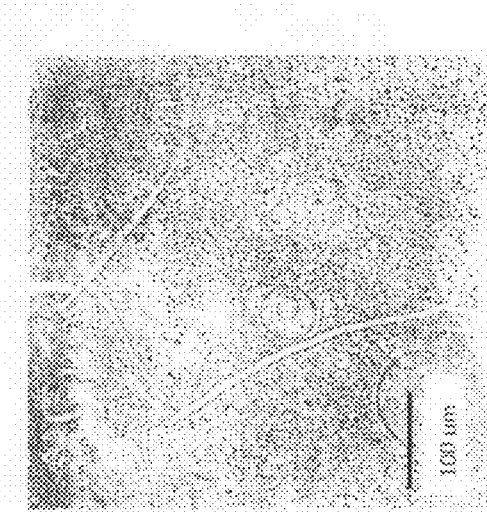
FIG. 10 is an SEM image of cross-linked agglomerations.

For electrospraying, the tip of the needle 104 and the grounded plate 108 can be placed closer together as compared to the described electrospinning method. Such positioning can result in the protein solution exiting the needle 104 and forming droplets of solution prior to entering the cross-linking solution in the receptacle 106. Such droplets internally cross-link once entering the cross-linking solution and form spherical protein agglomerates or beads. Protein agglomerates formed by electrospraying are shown in FIG. 10. Such protein agglomerates can be, for example, approximately 2 to 3 micrometers in diameter.

Figure 11:
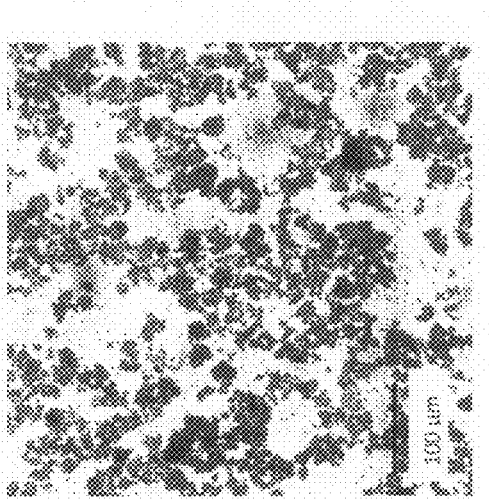
FIG. 11 is an SEM image of cross-linked agglomerations.

For a gravitation feed method, no electrical potential is needed. Gravity is used to draw beads of protein solution from the needle 104. The beads fall into the cross-linking solution and internally cross-link forming generally spherical protein agglomerates. Alternatively, each bead can break up into smaller beads upon impact with the surface of the cross-linking solution. Protein agglomerates formed by the gravitational feed method are shown in FIG. 11. Such protein agglomerates can be, for example, approximately 20 to 30 micrometers in diameter.

Parameters such as the distance between the tip of the needle 104 and the metal plate 108, flow rate of protein solution from the needle 104, voltage applied to the needle 104, concentration of protein in the protein solution, concentration of salt in the protein solution, and ratio of alcohol to water in the protein solution can affect the size of protein agglomerates or beads. However, for comparatively similar parameters, electrospraying can produce the smallest protein agglomerates, gravity feed can produce protein agglomerates larger than electrospraying, and electrospinning can produce protein agglomerates larger than the gravitational feed method.

Figure 12A:
FIG. 12A is an SEM image of a cross-linked protein film.
Figure 12B:
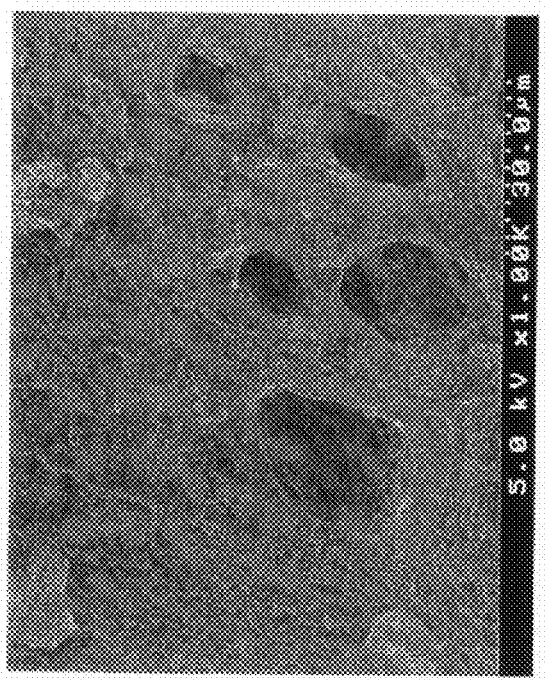
FIG. 12B is an SEM image of a cross-linked protein film.

Protein dissolved in benign solvents as described herein can be used to form porous protein films, scaffolds and gels. In one example, a protein solution can be deposited in a receptacle so that the protein solution covers the bottom of the receptacle. A solution that includes a cross-linking agent such as EDC in ethanol is poured over the protein solution. In one example, the cross-linking solution comprises about 0.2 millimoles of EDC. The receptacle can be hermetically covered for a period of time, for example about 24 hours. Evaporation of the solution results in a protein film forming on the bottom of the receptacle. Some salt crystals may be present on the surface of the film. Such salt crystals can be removed by washing the film with deionized water, which can leach out the salt. Once the salt is leached out, the film is left with a porous structure that includes numerous pores that intersect forming a protein structure with an open network of pores. FIGS. 12A and 12B show porous films formed from the described method. The porous structure of the film can include pores that range from submicron in size to over 30 micrometers in size.

Such a film with intersection pores can be suitable as a scaffold for cell repopulation or tissue growth. It will be understood that the intersecting pores mimic the ECM structure of human tissue and provide expanded surfaces on which cells and tissue can grow.

Figure 13B:
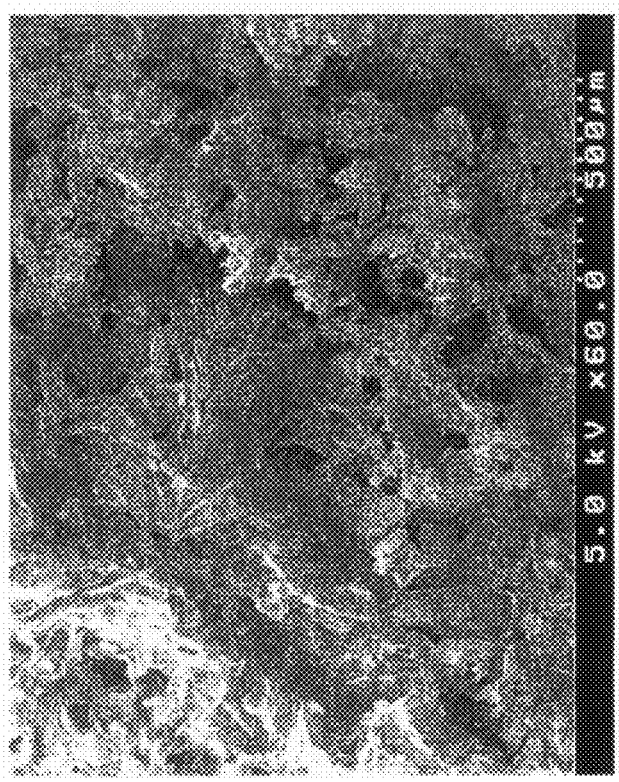
FIG. 13B is an SEM image of a protein structure with an open network of pores.
Figure 13A:
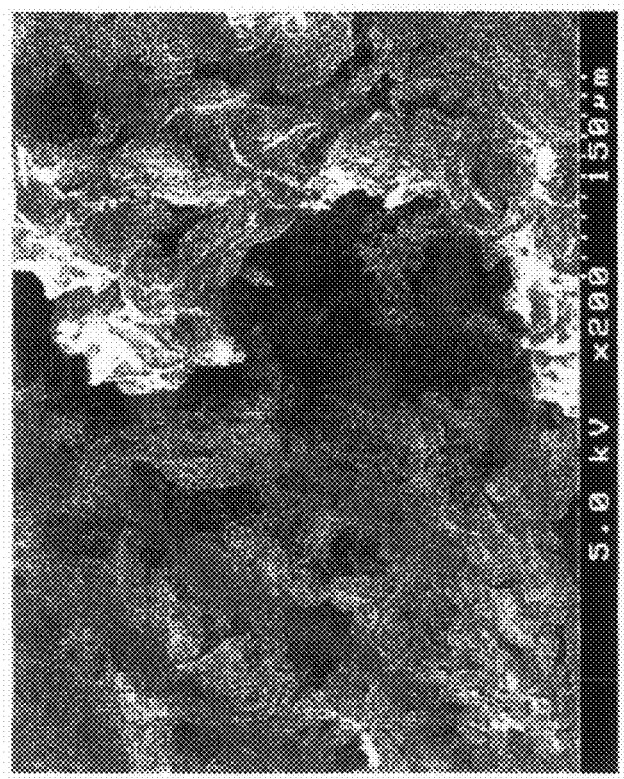
FIG. 13A is an SEM image of a protein structure with an open network of pores.

An example of another method of forming a protein structure with an open network of pores is hereafter described. A protein solution as described herein is prepared in a receptacle and stirred. As the protein solution is stirred, a cross-linking solution including a cross-linking agent such as EDC is deposited in the receptacle. Stirring continues until a protein cross-links and forms a gel in the receptacle. Once cross-linked the protein gel can be rinsed with deionized water to remove salts and alcohol from the gel. The gel is quenched in liquid nitrogen and frozen. The gel is placed in a vacuum chamber and water in or on the gel sublimes or otherwise evaporates. Such a method results in a low density protein scaffold with foam-like properties and an open network of pores. FIGS. 13A and 13B show a scaffold with an open network of pores formed from the described method. The pores as shown range in size from about 10 micrometers to about 50 micrometers. The size of the pores can be controlled by varying the protein content in the protein solution and the buffer to alcohol ratios.

The foregoing description of examples has been presented for purposes of illustration and description. It is not intended to be exhaustive or limiting to the forms described. Numerous modifications are possible in light of the above teachings. Some of those modifications have been discussed, and others will be understood by those skilled in the art. The examples were chosen and described in order to best illustrate principles of various examples as are suited to particular uses contemplated. The scope is, of course, not limited to the examples set forth herein, but can be employed in any number of applications and equivalent devices by those of ordinary skill in the art.

What is claimed is:

1. A method for forming a protein structure from a benign solvent comprising:
   forming a benign solvent from water, alcohol, and salt;
   dissolving a collagen in the benign solvent to form a collagen solution;
   extracting the collagen from the collagen solution; and
   arranging the collagen into a collagen structure.

2. The method of claim 1, further comprises electrospinning the collagen solution to extract collagen from the collagen solution.

3. The method of claim 1, further comprises electrospraying the collagen solution to extract collagen from the collagen solution.

4. The method of claim 1, further comprises using a gravitational feed method to extract collagen from the collagen solution.

5. The method of claim 1, wherein the collagen structure is a plurality of collagen fibers.

6. The method of claim 5, further comprising:
   forming at least some of the plurality of collagen fibers into a matrix;
   restraining the matrix; and
   placing the matrix in contact with alcohol.

7. The method of claim 5, further comprising aligning the plurality of collagen fibers.

8. The method of claim 1, further comprising:
   extracting the collagen from the collagen solution in the form of fibers; and
   applying a solution to the fibers to cross-link the fibers to form the collagen structure.

9. The method of claim 8, wherein the cross-linking solution comprises 1-ethyl-3-(3-dimethylaminopropyl)carbodiimide hydrochloride.

10. The method of claim 8, wherein the cross-linking solution comprises N-hydroxysuccinimide.

11. The method of claim 1, where in the collagen structure is a film.

12. The method of claim 11, further comprising placing the extracted collagen in contact with an alcohol to form the film.

13. The method of claim 1, wherein the collagen structure is at least one agglomerate.

14. The method of claim 13, wherein the at least one agglomerate is between about 2 micrometers and about 30 micrometers.

15. The method of claim 1, wherein the benign solvent comprises:
   a ratio of between about ninety-five to one and about five to ninety-five of water to alcohol by volume;
   a salt concentration of between about 0 moles per liter and about 13 moles per liter of salt; and
   the collagen solution comprises between about 1 percent and about 25 percent collagen by weight as compared to the benign solvent.

16. The method of claim 15, wherein:
   the ratio of water to alcohol is about one-to-one
   the salt concentration is about 3 moles per liter; and
   the collagen solution comprises about 16 percent collagen by weight as compared to the benign solvent.

17. The method of claim 15, wherein the alcohol is ethanol and the salt is predominantly sodium chloride.

18. The method of claim 1, wherein the benign solvent comprises phosphate buffered saline buffer and ethanol.

19. The method of claim 18, wherein the saline concentration of the buffer is between about 1× and about 20×.

20. The method of claim 19, wherein a ratio of buffer to ethanol is between about ninety-five to one and about five to ninety-five; and
   the collagen solution comprises between about 1 percent and about 25 percent collagen by weight as compared to the buffer and ethanol.

21. A method for forming a protein structure from a benign solvent comprising:
   forming a benign solvent from water, alcohol, and salt;
   dissolving a gelatin in the benign solvent to form a gelatin solution;
   extracting the gelatin from the gelatin solution; and
   arranging the gelatin into a gelatin structure.

22. The method of claim 21, wherein the gelatin structure is a plurality of gelatin fibers.

23. The method of claim 22, further comprising:
   forming at least some of the plurality of gelatin fibers into a matrix;
   restraining the matrix; and
   placing the matrix in contact with alcohol.

24. The method of claim 22, further comprising aligning the plurality of gelatin fibers.

25. The method of claim 21, where in the gelatin structure is a film.

26. The method of claim 25, further comprising placing the extracted gelatin in contact with an alcohol to form the film.

27. The method of claim 21, wherein the gelatin structure is at least one agglomerate.

28. The method of claim 27, wherein the at least one agglomerate is between about 2 micrometers and about 30 micrometers.

29. The method of claim 21, further comprises electrospinning the gelatin solution to extract gelatin from the gelatin solution.

30. The method of claim 21, further comprises electrospraying the gelatin solution to extract gelatin from the gelatin solution.

31. The method of claim 21, further comprises using a gravitational feed method to extract gelatin from the gelatin solution.

32. The method of claim 22 further comprising:
   extracting the gelatin from the gelatin solution in the form of fibers; and
   applying a solution to the fibers to cross-link the fibers to form the gelatin structure.

33. The method of claim 32, wherein the cross-linking solution comprises 1-ethyl-3-(3-dimethylaminopropyl)carbodiimide hydrochloride.

34. The method of claim 32, wherein the cross-linking solution comprises N-hydroxysuccinimide.

35. The method of claim 21, wherein the benign solvent comprises:
   a ratio of between about ninety-five to one and about five to ninety-five of water to alcohol by volume;
   a salt concentration of between about 0 moles per liter and about 13 moles per liter of salt; and
   the gelatin solution comprises between about 1 percent and about 25 percent gelatin by weight as compared to the benign solvent.

36. The method of claim 35, wherein:
   the ratio of water to alcohol is about one-to-one
   the salt concentration is about 3 moles per liter; and the gelatin solution comprises about 16 percent gelatin by weight as compared to the benign solvent.

37. The method of claim 35, wherein the alcohol is ethanol and the salt is predominantly sodium chloride.

38. The method of claim 21, wherein the benign solvent comprises phosphate buffered saline buffer and ethanol.

39. The method of claim 38, wherein the saline concentration of the buffer is between about 1× and about 20×.

40. The method of claim 39, wherein a ratio of buffer to ethanol is between about ninety-five to one and about five to ninety-five; and the gelatin solution comprises between about 1 percent and about 25 percent gelatin by weight as compared to the buffer and ethanol.

* * * * *